(12) United States Patent
Kniajanski et al.

(10) Patent No.: US 7,652,157 B2
(45) Date of Patent: Jan. 26, 2010

(54) METAL OXIDE COATINGS

(75) Inventors: Sergei Kniajanski, Clifton Park, NY (US); Aharon Yakimov, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 11/931,039

(22) Filed: Oct. 31, 2007

(65) Prior Publication Data

US 2008/0319212 A1 Dec. 25, 2008

Related U.S. Application Data

(60) Provisional application No. 60/945,715, filed on Jun. 22, 2007.

(51) Int. Cl.
C07F 7/26 (2006.01)
(52) U.S. Cl. .......................... 556/10; 556/173; 556/450
(58) Field of Classification Search ................. 556/400
See application file for complete search history.

(56) References Cited

U.S. PATENT DOCUMENTS 4,525,565 A 6/1985 Laisney et al.
2004/0086643 A1 5/2004 Onozawa et al.

FOREIGN PATENT DOCUMENTS

| EP | 1621258 A1 | | 2/2006 |
|----|------------|---|--------|
| GB | 2428689 A | | 2/2007 |
| JP | 09048787 | * | 2/1997 |
| JP | 2003165841 | * | 6/2003 |
| RU | 2064956 | * | 8/1996 |

OTHER PUBLICATIONS

Sakharovskaya et al, {Synthesis and some properties of polyaluminoorganosiloxanes, Plasticheskie Massy (1966), (10), 23-25, Abstract}.*
Andrianov et al, "Titanodimethylsiloxane Oligomers", CAN 64:35960.

* cited by examiner

Primary Examiner—Daniel M Sullivan
Assistant Examiner—Chukwuma O Nwaonicha

(74) Attorney, Agent, or Firm—Mary Louise Gioeni

(57) ABSTRACT

Compounds of formula I may be hydrolyzed to produce metal oxides

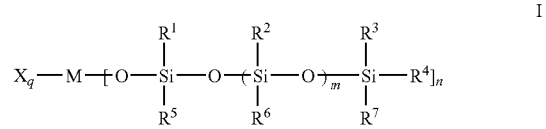

wherein
M is Mg, Al, Ca, Sc, Ti, V, Cr, Mn, Fe, Co, Ni, Cu, Zn, Ga, Ge, As, Y, Zr, Nb, Mo, Tc, Ru, Rh, Pd, Cd, In, Sn, Sb, La, Hf, Ta, W, Re, Os, Ir, Pt, Hg, Tl, Pb, Bi, Ce, Pr, Nd, Sm, Eu, Gd, Tb, Dy, Ho, Er, Tm, Yb, Lu, Th, U, or Pu;
X is $O_{1/2}$ or OR;
R is alkyl;
$R^1$, $R^2$, $R^3$, $R^4$, $R^5$, $R^6$, and $R^7$ are independently H, alkoxy, $C_1$-$C_{10}$ alkyl, phenyl or

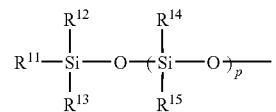

$R^{10}$, $R^{11}$, $R^{12}$, $R^{13}$, $R^{14}$ and $R^{15}$ are independently $C_1$-$C_{10}$ alkyl or phenyl;
n is equal to the the value of the oxidation state of M minus q;
m and p are independently 0 or an integer from 1 to 5; and
q is 0, 1, 2, or 4;
with the proviso that
when q is 1, X is OR; and
when q is 2, X is $O_{1/2}$, and M is V, Cr, Mn, Fe, As, Nb, Mo, Tc, Ru, Sb, Ta, W, Re, Os, Ir, Pt, Bi, Th, U, or Pu; and
when q is 4, X is $O_{1/2}$, and M is Cr, Mo, W, Ru, Re, Os, U, or Pu.

Articles comprising at least one metal oxide are fabricated by coating a substrate with at least one compounds of formula I before hydrolyzing, and/or heating the compound at a temperature ranging from about 50° C. to about 450° C.

11 Claims, No Drawings

METAL OXIDE COATINGS

CROSS REFERENCE TO RELATED APPLICATIONS

This application is a non-provisional of and claims priority from U.S. Provisional Patent Application Ser. No. 60/945,715, filed on Jun. 22, 2007, the entire contents of which is incorporated herein by reference.

BACKGROUND

Transparent conductive oxides (TCO) are electronic materials that find utilization in a large variety of optoelectronic devices including, but not limited to flat panel displays, liquid crystal displays, plasma displays, electroluminescent displays, touch panels and solar cells. These materials also used as antistatic coatings and electro-magnetic interference (EMI) shielding. TCOs are of crucial importance for a number of emerging technologies, such as organic electroluminescent devices (both displays and lighting devices), photovoltaic (PV) devices, including crystalline-Si heterojunction with intrinsic thin layer, amorphous silicon, CdTe, CuIn(Ga)$Se_2$ (CIGS), and organic photovoltaics. TCOs act as transparent conducting windows, structural templates, and diffusion barriers TCOs are also used for various optical coatings, in particular as infra-red reflecting coatings (heat mirrors) in automotive and building industries. Although the main desirable characteristics of TCO materials are common to many technologies, including high optical transmissivity across a wide range of light spectrum and low electrical resistivity, specific TCO parameters vary from one system to another. Emerging technologies require new types of transparent conductors with properties better adjusted to their needs. The number of compositions currently used as TCOs is restricted to a few primary and binary systems. This is mainly because of two factors: 1) limited bulk solubility of crystalline metal oxide phases in each other, and 2) certain technical limitations of the currently used methods. If these challenges could be overcome, it has been shown that the number of suitable transparent and conductive binary, ternary and even quaternary phases may be larger (A. J. Freeman, K. R. Poeppelmeier, T. O. Mason, R. P. H. Chang, and T. J. Marks, MRS Bulletin, 45-51, August 2000). Some of them may potentially exist in thin films only since the phase separation in this case is kinetically precluded by the film thinness.

A convenient way to make a large variety of multicomponent TCOs is low-pressure or high-pressure CVD using solid volatile organometallic precursors. However, CVD requires high substrate temperature (400-450° C.) needed for precursor decomposition. Despite the fact that this method can be applied for large area production, it is limited to thermally stable substrates (like glass and metal foils) and cannot be applied for direct TCO layer deposition onto such light absorbers as CIGS, CdTe, and organic PVs.

TCO's are commercially fabricated by magnetron sputtering. Other physical deposition techniques (electron beam evaporation, pulsed laser deposition, etc.) can also be applied. It is widely recognized that sputtering provides the best results in terms of high optical transparency and electrical conductivity of metal-oxide films, particularly ITO, ZnO, and $ZnO—Al_2O_3$. However, expensive vacuum equipment, high energy consumption (~30 $kW/m^2$), and batch production all contribute into the high technology cost. Additionally, PVD technologies impose certain limitations on the development of multicomponent (more than two) TCOs because of technical difficulties in controlling uniform element distribution, and thus the consistency of material properties, over time. As a result, PVD methods are not well suited for development of new TCO formulations for emerging PV systems. The progress in this area is a subject of method versatility and flexibility.

Accordingly, there is a need for solution-based technologies, which have the additional benefit of process cost reduction, as compared to PVD, being well suited for fast continuous roll-to-roll fabrication.

Solution-based preparation of different parts of PV devices (amorphous silicon layer, CIGS layer, organic PVs, CdS junction layer, TCO) has recently been the subject of intensive research. While noticeable progress has been achieved by both academia and industry in high-throughput fabrication of various PV components, suitable solution-based low-temperature TCO production remains a challenge and could be the ultimate barrier to fully solution-processed PVs. A considerable amount of effort has been devoted to developing printed TCOs. Despite certain progress in this field, none of the commercialized materials are used for PV devices mostly because of inferior conductivity-transparency properties when compared to those TCO's produced by sputtering. Known wet methods have limitations, which preclude them from reaching the goals imposed by PV technologies: sheet resistance of <7 Ω/, optical transmissivity >90% in near UV-visible-near IR regions of light spectrum, and low haze.

A number of approaches have been tried to fabricate TCOs by wet processes. Sol-gel processes are relatively slow, proceeding via a porous sediment formation and requiring high temperature for the film crystallization and densification. The chemical nature of this process does not allow for fabrication of high quality TCO. Metal-organics decomposition can be done relatively fast, but like CVD, requires high temperature for precursor degradation. This method starts from the deposition of a dilute solution or a slurry of precursor(s) in a liquid carrier, and results in the formation of porous films. Nanosolution inks for ITO fabrication have been widely commercialized for low-end applications. Their use for PV devices is still far from reality, first because of high temperature needed for sintering nano-particles, and second, because of insufficient conductivity-transparency performance. The latter is an inherent problem of sintering process, since the boundaries between the original particles cannot be completely eliminated at temperatures below 450° C. These boundaries are the reason for low carrier concentration, low charge mobility, and high haze. Oxidative spray pyrolysis is widely used for FTO (fluorinated tin oxide) and ATO (antimony-tin oxide) fabrication. It can be also used for ZnO, and possibly for other TCOs. Besides high temperature (450-550° C.) requirements, this method is not capable of high-end TCO film fabrication.

Thus, a versatile, flexible, low temperature, low cost wet process for fabrication of a wide variety of TCOs is desirable. Such a process would not only allow reduced TCO cost and fabrication of flexible devices, but also TCOs with properties that may be better adjusted for particular technology needs, resulting in improved device efficiency.

SUMMARY

In one aspect, the present invention relates to compounds of formula I

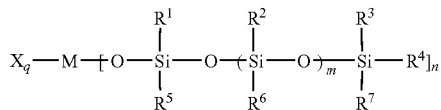

I wherein

M is Mg, Al, Ca, Sc, Ti, V, Cr, Mn, Fe, Co, Ni, Cu, Zn, Ga, Ge, As, Y, Zr, Nb, Mo, Tc, Ru, Rh, Pd, Cd, In, Sn, Sb, La, Hf, Ta, W, Re, Os, Ir, Pt, Hg, Tl, Pb, Bi, Ce, Pr, Nd, Sm, Eu, Gd, Tb, Dy, Ho, Er, Tm, Yb, Lu, Th, U, or Pu;

X is $O_{1/2}$ or OR;

R is alkyl;

$R^1$, $R^2$, $R^3$, $R^4$, $R^5$, $R^6$, and $R^7$ are independently H, alkoxy, $C_1$-$C_{10}$ alkyl, phenyl or

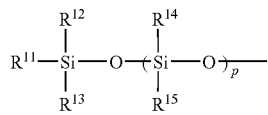

$R^{10}$, $R^{11}$, $R^{12}$, $R^{13}$, $R^{14}$ and $R^{15}$ are independently H, $C_1$-$C_{10}$ alkyl or phenyl;

n is equal to the value of the oxidation state of M minus q;

m and p are independently 0 or an integer from 1 to 5; and q is 0, 1 2, or 4;

with the proviso that when q is 1, X is OR;

when q is 2, X is $O_{1/2}$, and M is Ti, V, Mn, Nb, Mo, Tc, Ru, Sb, Ta, W, Re, Os, Th, or U; and when q is 4, X is $O_{1/2}$, and M is Cr, Mo, W, Ru, Re, Os, U, or Pu.

The metallic center of the compounds of formula I may be optionally coordinated with a Lewis base such as acyclic or cyclic ethers, amines, phosphines, arsines, or sulfides. For example, Zn compounds, some of which are solid in non-coordinated forms, may be liquids when complexed with ether, THF, or triethylamine.

In another aspect, the present invention relates to processes for fabricating an article comprising at least one metal oxide by hydrolyzing at least one compound of formula I. The process may additionally include coating a substrate with the compound before hydrolyzing, and/or heating the compound at a temperature ranging from about 50° C. to about 450.

Advantages of the process of the present invention include: relatively inexpensive starting materials, relatively low process temperatures, low process cost, high quality film formation, ability to fabricate multicomponent films, applicability to a variety of substrates because of good wetting properties of the compounds of formula I, printability, exact control of component stoichiometry, and easy tunability of process parameters and material properties.

Metal trialkylsilyloxy derivatives of formula $M(OSiMe_3)_x$, where M is Ti, Zr, Nb, Tl, Hf, Sn, and Al, and x is the value of the valence of M, are known (*Journal of the Chemical Society*, (1959), 3404-11; *Chemistry & Industry* (1958), 17) Tetrakis(trimethylsiloxy)titanium has been hydrolyzed in dioxane to yield poly(trimethylsiloxano-titanoxanes) (*Canadian J. Chemistry* (1963), 41 629-35). These materials typically do not produce uniform films when applied directly to a substrate or from solution.

DETAILED DESCRIPTION

The present invention relates to compounds of formula I, and their use in preparing metal oxides. Embodiments of the compounds of formula I include metal siloxanolates (where q is 0) of formula

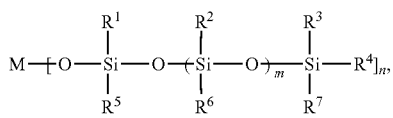

metal alkoxide siloxanolates (where q is 1) of formula

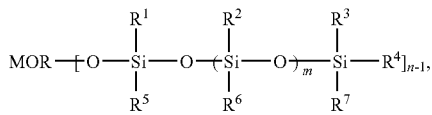

metal oxide siloxanes (where q is 2) of formula

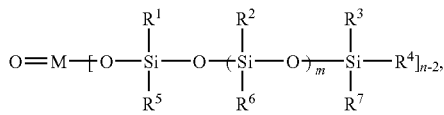

and metal oxide siloxanes (where q is 4) of formula

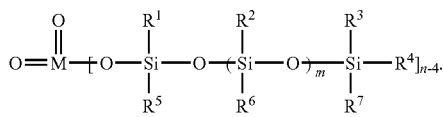

In particular embodiments the compounds of the present invention are of formula

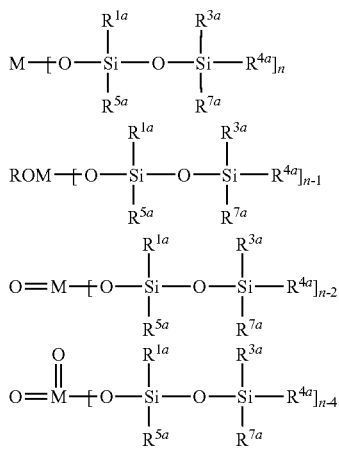

wherein $R^{1a}$, $R^{3a}$, $R^{4a}$, $R^{5a}$, and $R^{7a}$ are H or $C_1$-$C_{10}$ alkyl, preferably methyl.

For many embodiments of the present invention, preferred substituents ($R^{1-7}$ and $R^{1a-7a}$) for the compounds are $C_1$-$C_{10}$ alkyl; more preferred is methyl. Preferred metals are Mg, Al, Sc, Ti, V, Zn, Ga, Y, Zr, Mo, Cd, In, Sn, Sb, Ce, Gd, Lu, and W. More preferred metals are Al, Ga, Sc, Y, Ti, V, Zn, Cd, In, Sb and Sn.

Specific embodiments of the compounds of formula I include $Ti(OSi(CH_3)_2OSi(CH_3)_3)_4$, $Al(OSi(CH_3)_2OSi(CH_3)_3)_3$, $Ga(OSi(CH_3)_2OSi(CH_3)_3)_3$, $VO(OSi(CH_3)_2OSi(CH_3)_3)_3$, $Zn(OSi(CH_3)_2OSi(CH_3)_3)_2$, $Sn(OSi(CH_3)_2OSi(CH_3)_3)_4$, and $In(OSi(CH_3)_2OSi(CH_3)_3)_3$.

Methods for preparing the compounds of formula I include the following reactions:

$$X_qM(OR)_n + n\ ZOAc \Rightarrow X_qM(OZ)_n + n\ ROAc \quad (1)$$

wherein Z is

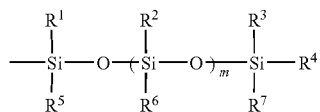

M, R, $R^1$—$R^7$, m, q and n are as defined above.

Metals for which compounds of formula I may be prepared via reaction 1 include, for example, Zn, Al, In, Ti, Zr, V, Ga, Sc, Y, La, the lanthanides, Bi(III), and especially Zn, Al, In, Ti, Zr, and V. Exemplary R groups include ispropyl and n-butyl.

$$MX^1{}_n + n\ ZOH + n\ NR_3 \rightarrow M(OZ)_n + nNR_3H + X— \quad (2)$$

wherein M and Z are as defined above, $X^1$ is halo, and $NR_3$ is any alicyclic, cyclic or polycyclic amine which easily forms a hydrochloride salt, such as trialkylamines, pyridine, hexamethylenediamine.

Metals for which compounds of formula I may be prepared via reaction 2 include, for example, Sn(IV), Pb(IV), Sb(V), Nb(V), and Ta(V), especially Sn.

$$MR_n + nZOH \rightarrow M(OZ)_n + nRH \quad (3)$$

wherein M, R, n, and Z are as defined above.

Metals for which compounds of formula I may be prepared via reaction 3 include, for example, Mg, Zn, In, Al, Ga and Hg. Examples of compounds of formula $MR_n$ that may be used in reaction 3 include $MgBu_2$, $ZnEt_2$, $InBu_3$, $AlBu_3$, $GaBu_3$, $HgMe_2$. Exemplary R groups include ethyl and butyl.

The compounds of the present invention are typically liquids with excellent wetting properties on substrates of interest and/or soluble in common organic solvents and may be conveniently applied by common coating methods. In addition, they are typically stable in dry air at room temperature, so they may be handled without any special precautions. When exposed to humid air at elevated temperatures, typically 50° C.-450° C., preferably 100° C.-200° C., the compounds are converted into metal oxides by hydrolysis with atmospheric moisture and/or thermal disproportionation. Byproducts are volatile low molecular weight siloxanes, which may be easily sequestrated.

Accordingly, in another aspect, the present invention relates to a process for fabricating an article that includes a metal oxide, by hydrolyzing a compound of formula I. The metal oxides include monometallic and polymetallic oxides and doped oxide matrix systems, including, for example, ZnO, CdO, $In_2O_3$, $SnO_2$, $Al_2O_3$, $Ga_2O_3$, and $Sb_2O_5$, binary, ternary, and quaternary oxides based thereon, and the matrix-dopant systems listed in Table 1.

TABLE 1

| Matrix | Dopant or Compound |
|---|---|
| ZnO | Al, Y, Sc, Ti, Zr |
| ZnO—$SnO_2$ | $Zn_2SnO_4$, $ZnSnO_3$ |
| $SnO_2$ | $BaSnO_3$, $SrSnO_3$, Sb |
| $TiO_2$ | $BaSnO_3$, $SrSnO_3$, V |
| $In_2O_3$ | Zn, Sn, Ga, Al |

Preferred metal oxides are TCOs. Oxides that include more than one metallic element may be prepared by combining one or more compounds of formula I and hydrolyzing the mixture.

In the process of the present invention, the compounds of formula I are hydrolyzed by heating at a temperature ranging from about 50° C. to about 450° C. in the presence of water vapor. Relative humidity typically ranges from about 5% to about 100%, preferably from about 5% to about 75%, and more preferably from about 10% to about 55%. Very little water is typically required, as other reactions that produce metal oxides and/or water may occur during the process. For example, dimerization of siloxanols released by the hydrolysis reaction may yield water, which can hydrolyze additional metal-ligand bonds (equations 4 and 5).

$$M(OSiMe_2OSiMe_3)_n + 2\ H_2O \rightarrow MO_n + n\ Me_3SiOSiMe_2OH \quad (4)$$

$$4\ Me_3SiOSiMe_2OH \rightarrow 2\ Me_3SiOSiMe_2OSiMe_2OSiMe_3 + 2\ H_2O \quad (5)$$

Metal-siloxane derivatives may undergo thermal rearrangement by reaction (6) without added water.

$$M(OSiMe_2OSiMe_3)_n \rightarrow MO_n + Me_3SiOSiMe_2OSiMe_2OSiMe_3 \quad (6)$$

Thermal rearrangement with the formation of metal-methyl bond and unstable siloxanone (reaction 7) may also yield metal-alkyl fragments that may be hydrolyzed even faster than metal siloxanolates.

$$M(OSiMe_2OSiMe_3)_n \rightarrow MMe(OSiMe_2OSiMe_3)_{n-1} + Me_3SiOSi(Me){=}O \quad (7)$$

Acid catalysts may also increase the rate of the hydrolysis. Suitable acids include organic acids such as acetic acid, propionic acid and butyric acid. The amount of acid typically ranges from about 0.01 ppm to about 1000 ppm, based on total weight, preferably from about 0.1 ppm to about 10 ppm.

The process of the present invention may additionally include coating a substrate with the compounds of formula I before hydrolyzing. Substrates for use in the process are only limited by their suitability for the end use, and may include glass, ceramics, plastics, metals, alloys, wood, paper, graphite, textiles, organic or inorganic substrates, such as various components of optical, electronic, or opto-electronic devices. Any method for producing a thin film on a substrate may be used, including conventional coating methods such as, but not limited to spin coating, dip coating, spray coating, and printing techniques, such as screen printing, ink-jet printing, gravure and rotogravure printing, flexography, offset printing, laser printing and pad printing. The coating or printing method and its parameters may affect properties of the film, such as thickness and uniformity, and may be adjusted to achieve a desired result. Parameters that may be adjusted may include, for example, type of solvent, precursor concentration, material amount, spin rate and spin time (for spin-coating), residence time (dipping and spray), and other relevant parameters, as will be apparent to the skilled in the art.

The compounds of formula I may be applied as neat liquids where applicable, in solvents or solvent mixtures that are relatively volatile at process temperatures. The solvent may affect both hydrolysis kinetics and film properties. Polar and water miscible solvents may promote faster hydrolysis. Suitable solvents include alkanes such as hexanes, heptane, and octane; aromatics such as benzene, toluene, xylenes; dialkyl ethers such as dipropyl ether, diisopropyl ether, di-t-butyl ether, and dibutyl ether, monoglyme, and diglyme; cyclic ethers such as 1,4-dioxane, 1,3-dioxane, furan, tetrahydrofuran, pyran, tetrahydropyran, and the like; ketones such as acetone, methylethylketone, cyclohexanone; dimethylformamide, demethylacetamide, and mixtures thereof. Preferred solvents are hexanes, toluene and dimethylformamide. A suitable amount of water, preferably purified water, may be added to the solution if desired in any manner, prior to, during, or subsequent to the preparation of the solution.

Where the substrate is heat-resistant, an additional annealing step may be performed. Annealing temperature ranges from about 200° C. to about 450° C.

Due to their good wetting properties, the compounds of formula I typically form uniform continuous liquid films on substrates. After hydrolysis/thermolysis and, if desired, annealing, they are converted into thin uniform metal oxide films. Adhesion of the films to the substrate may depend on the substrate nature and film thickness, but is typically good for films thinner than 0.5 microns.

The process of the present invention provides articles that include metal oxide coatings, particularly articles that include conductive or semiconductive metal oxide coatings, particularly thin film coatings which, depending on the nature of metal oxide, have high refractive index, high catalytic/photocatalytic activity, electrically conductive or semiconductive properties, non-linear optical properties, switching properties, barrier properties, and/or binding properties. The process may be used for production of transparent semiconductors and electrodes, sensors, high refractive index surfaces, such as windows, optics, ceramics, elements with non-linear optical properties, anti-reflective coatings, self-cleaning windows, elements with catalytic properties for NOx reduction and/or removing sulfur from oil and fuels, protective coatings, anti-corrosion coatings, anti-static coatings, and barrier coatings for excluding organics, moisture, and/or gases. The process may also be used for fabricating transparent electrodes for photovoltaic devices, flat panel displays, touch panels, OLEDs, gradient refractive index layers in LED lamps and OLEDs, hole plugging in solid state fuel cell blocks, binding preformed metal oxide powders, such as titania reflective coatings, and dye sensitized solar cells. Final properties of the coatings depend on the nature of the metal oxide.

In the context of the present invention, alkyl is intended to include linear, branched, or cyclic hydrocarbon structures and combinations thereof, including lower alkyl and higher alkyl. Preferred alkyl groups are those of $C_{20}$ or below. Lower alkyl refers to alkyl groups of from 1 to 6 carbon atoms, preferably from 1 to 4 carbon atoms, and includes methyl, ethyl, n-propyl, isopropyl, and n-, s- and t-butyl. Higher alkyl refers to alkyl groups having seven or more carbon atoms, preferably 7-20 carbon atoms, and includes n-, s- and t-heptyl, octyl, and dodecyl. Cycloalkyl is a subset of alkyl and includes cyclic hydrocarbon groups of from 3 to 8 carbon atoms. Examples of cycloalkyl groups include cyclopropyl, cyclobutyl, cyclopentyl, and norbornyl. Alkenyl and alkynyl refer to alkyl groups wherein two or more hydrogen atoms are replaced by a double or triple carbon-carbon bond, respectively.

Aryl and heteroaryl mean a 5- or 6-membered aromatic or heteroaromatic ring containing 0-3 heteroatoms selected from nitrogen, oxygen or sulfur; a bicyclic 9- or 10-membered aromatic or heteroaromatic ring system containing 0-3 heteroatoms selected from nitrogen, oxygen or sulfur; or a tricyclic 13- or 14-membered aromatic or heteroaromatic ring system containing 0-3 heteroatoms selected from nitrogen, oxygen or sulfur. The aromatic 6- to 14-membered carbocyclic rings include, for example, benzene, naphthalene, indane, tetralin, and fluorene; and the 5- to 10-membered aromatic heterocyclic rings include, e.g., imidazole, pyridine, indole, thiophene, benzopyranone, thiazole, furan, benzimidazole, quinoline, isoquinoline, quinoxaline, pyrimidine, pyrazine, tetrazole and pyrazole.

Arylalkyl means an alkyl residue attached to an aryl ring. Examples are benzyl and phenethyl. Heteroarylalkyl means an alkyl residue attached to a heteroaryl ring. Examples include pyridinylmethyl and pyrimidinylethyl. Alkylaryl means an aryl residue having one or more alkyl groups attached thereto. Examples are tolyl and mesityl.

Alkoxy or alkoxyl refers to groups of from 1 to 8 carbon atoms of a straight, branched, cyclic configuration and combinations thereof attached to the parent structure through an oxygen. Examples include methoxy, ethoxy, propoxy, isopropoxy, cyclopropyloxy, and cyclohexyloxy. Lower alkoxy refers to groups containing one to four carbons.

Acyl refers to groups of from 1 to 8 carbon atoms of a straight, branched, cyclic configuration, saturated, unsaturated and aromatic and combinations thereof, attached to the parent structure through a carbonyl functionality. One or more carbons in the acyl residue may be replaced by nitrogen, oxygen or sulfur as long as the point of attachment to the parent remains at the carbonyl. Examples include acetyl, benzoyl, propionyl, isobutyryl, t-butoxycarbonyl, and benzyloxycarbonyl. Lower-acyl refers to groups containing one to four carbons.

Heterocycle means a cycloalkyl or aryl residue in which one to two of the carbons is replaced by a heteroatom such as oxygen, nitrogen or sulfur. Examples of heterocycles that fall within the scope of the invention include pyrrolidine, pyrazole, pyrrole, indole, quinoline, isoquinoline, tetrahydroisoquinoline, benzofuran, benzodioxan, benzodioxole (commonly referred to as methylenedioxyphenyl, when occurring as a substituent), tetrazole, morpholine, thiazole, pyridine, pyridazine, pyrimidine, thiophene, furan, oxazole, oxazoline, isoxazole, dioxane, and tetrahydrofuran.

Substituted refers to residues, including, but not limited to, alkyl, alkylaryl, aryl, arylalkyl, and heteroaryl, wherein up to three H atoms of the residue are replaced with lower alkyl, substituted alkyl, aryl, substituted aryl, haloalkyl, alkoxy, carbonyl, carboxy, carboxalkoxy, carboxamido, acyloxy, amidino, nitro, halo, hydroxy, $OCH(COOH)_2$, cyano, primary amino, secondary amino, acylamino, alkylthio, sulfoxide, sulfone, phenyl, benzyl, phenoxy, benzyloxy, heteroaryl, or heteroaryloxy.

Haloalkyl refers to an alkyl residue, wherein one or more H atoms are replaced by halogen atoms; the term haloalkyl includes perhaloalkyl. Examples of haloalkyl groups that fall within the scope of the invention include $CH_2F$, $CHF_2$, and $CF_3$.

Siloxy refers to saturated linear, branched or cyclic structures and combinations thereof, based on a backbone having alternating silicon and oxygen atoms, each silicon atom separated from its nearest silicon neighbors by single oxygen atoms and substituted with 0-3 hydrogen, halo, alkyl or aryl groups.

EXAMPLES

Example 1

Synthesis of $Ti(OSi(CH_3)_2OSi(CH_3)_3)_4$

Freshly distilled titanium isopropoxide (9 g, 31.66 mmol, Aldrich) was mixed with 250 ml of dry cyclohexane in a 500-ml three-neck round bottom flask equipped with a thermometer, addition funnel, magnetic stirring and a Liebig condenser attached to argon-vacuum line. The mixture was heated to 55-60° C., and 26.5 g of acetoxypentamethyldisiloxane (0.128 mol, used as purchased from Gelest Co., Morrisville Pa.) in 50 ml of dry cyclohexane were added dropwise during 1 hour under vigorous stirring. The mixture was heated to 55-60° C. for additional 2 hours and was allowed to cool down to room temperature. Volatiles were removed under reduced pressure. The residue was distilled at 80-82° C./0.05 torr to afford 13.5 g of colorless light liquid $Ti(OSi(CH_3)_2OSi(CH_3)_3)_4$. Refractive index ($n_D^{20}$) of $Ti(OSi(CH_3)_2 OSi(CH_3)_3)_4$ measured with Abbe refractometer at 25° C. was 1.413.

Example 2

Synthesis of $Al(OSi(CH_3)_2OSi(CH_3)_3)_3$

Aluminum isopropoxide (8.6 g, 42.11 mmol, from Gelest Co.) was dissolved in 250 ml of dry cyclohexane in a 500-ml three neck round bottom flask equipped with a thermometer, addition funnel, magnetic stirring and a Liebig condenser attached to argon-vacuum line. The mixture was heated to 55-60° C., and 26.5 g of acetoxypentamethyldisiloxane (0.128 mol) in 50 ml of dry cyclohexane were added dropwise during 1 hour under vigorous stirring. The mixture was heated to 55-60° C. for additional 2 hours and was allowed to cool down to room temperature. Volatiles were removed under reduced pressure. An oily residue was added dropwise to short-path distillation apparatus at 170-180° C./0.02 torr. 8.7 g of colorless oily $Al(OSi(CH_3)_2OSi(CH_3)_3)_3$ was obtained after distillation.

Example 3

Synthesis of $VO(OSi(CH_3)_2OSi(CH_3)_3)_3$

Vanadium triisopropoxide oxide (10.3 g, 42.18 mmol, Gelest Co.) was mixed with 250 ml of dry cyclohexane in a 500-ml three neck round bottom flask equipped with a thermometer, addition funnel, magnetic stirring and a Liebig condenser attached to argon-vacuum line. The mixture was heated to 55-60° C., and 26.5 g of acetoxypentamethyldisiloxane (0.128 mol) in 50 ml of dry cyclohexane were added dropwise during 1 hour under vigorous stirring. The mixture was heated to 55-60° C. for additional 2 hours and was allowed to cool down to room temperature. Volatiles were removed under reduced pressure. The residue was distilled at 40-42° C./0.015 torr to afford 12.2 g of yellowish light liquid $VO(OSi(CH_3)_2OSi(CH_3)_3)_3$.

Example 4

Synthesis of $Zn(OSi(CH_3)_2OSi(CH_3)_3)_2$

A 0.1 M solution of diethylzinc in heptane (40 ml, Aldrich) was transferred into a 500-ml three-neck round bottom flask equipped with a thermometer, addition funnel, magnetic stirring and a Liebig condenser attached to argon-vacuum line. Anhydrous ispraponol (6 ml, Aldrich) was slowly added under vigorous stirring. Additional 50 ml of anhydrous isopropanol were added and the mixture was refluxed for 1 hour. Volatiles were removed under reduced pressure affording white crystalline zinc isopropoxide, which was dried under vacuum at 80° C. for an hour. Dry cyclohexane (250 ml) was added into the flask, and the solid quickly dissolved. The mixture was heated to 55-60° C., and 17.0 g of acetoxypentamethyldisiloxane (82 mmol) in 50 ml of dry cyclohexane was added dropwise during 1 hour under vigorous stirring. The mixture was heated to 55-60° C. for additional 2 hours and was allowed to cool to room temperature. Volatiles were removed under reduced pressure. A solid waxy residue was dried under vacuum at 50° C., then was transferred into a sublimation apparatus, and was sublimed at 110° C./0.02 torr to afford 9.7 g of white solid $Zn(OSi(CH_3)_2OSi(CH_3)_3)_2$.

Example 5

Synthesis of $Me_3SOSiMe_2OH$

Pentamethyldisiloxane (25 g, 0.168 mol, Gelest Co.) was slowly added to 50 ml of monoglyme containing 3.5 g of water and 1 g of 10% Pd/C under vigorous stirring. After gas release had ceased, the mixture was dried with anhydrous $MgSO_4$ and filtered through a sintered glass filter. The filtrate was stirred with $CaH_2$ for 1 hour, and was distilled at 50° C. under reduced pressure. The content of pentamethyldisiloxanol in distillate was determined by 1H NMR analysis.

Example 6

Synthesis of $Sn(OSi(CH_3)_2OSi(CH_3)_3)_4$

A 1.0 M solution of $SnCl_4$ in heptane (20 ml, Aldrich) were dissolved in 300 ml of dry hexanes. Dry triethylamine (15 ml, 0.108 mol) was added, and the mixture was stirred for 10 min. 11.87 g of pentamethyldisiloxanol (0.08 mol, solution in monoglyme) were added in a few portions, and the mixture was stirred for 1 hour at room temperature. The mixture was filtered through a sintered glass filter, and the filtrate was refluxed for 1 hour. The mixture was cooled to room temperature and filtered again. Volatiles were removed under reduced pressure, and finally under vacuum. The residue was centrifuged to separate a dark-yellow heavy oil from supernatant colorless $Sn(OSi(CH_3)_2OSi(CH_3)_3)_4$, yield about 75%

Example 7

Synthesis of $In(OSi(CH_3)_2OSi(CH_3)_3)_3$ $InCl_3$ (10 g, 45.2 mmol, Aldrich) was dissolved in 150 ml of dry toluene. In order to remove traces of water coming with $InCl_3$, the solution was subjected to slow distillation under nitrogen until the point when the distillation temperature reached 108° C. The solution was cooled to 0° C. 68 ml of 1.0 M $Mg(Bu)_2$ solution in heptane (Aldrich) was slowly added to $InCl_3$ at 0° C. under vigorous stirring. After the addition was completed, the mixture was stirred for 2 hrs at 70° C. Solids were separated by filtration. The filtrate was distilled first at ambient pressure to remove the most part of solvents, and then at 0.1 torr. A fraction boiling at 70-72° C./0.1 mm Hg was collected. 12.1 g of InBu₃ were obtained. This material was dissolved in 200 ml of dry hexane, and 19 g of pentamethyl-disiloxanol (0.128 mol, solution in monoglyme) were slowly added to the reaction mixture. After the addition was completed, the mixture was stirred for 1 hour and then refluxed for additional 2 hours providing safe escape way for butane release. Volatiles were removed under reduced pressure. The residue was distilled as described for Al(OSi(CH₃)₂OSi(CH₃)₃)₃, yield >90%.

Examples 8-11

Preparation of Transparent Oxide-Coated Substrate

A 4-inch silicon wafer was spin-coated with 5 wt % solution of Ti(OSi(CH₃)₂OSi(CH₃)₃)₄ in hexane at 2 krpm/30 sec. The wafer was placed into a 150° C. oven for 1 hour. Refractive index ($n_D^{22}$) of the resulted coating measured with an ellipsometer was 1.721 at 30 nanometers thickness. After an additional 6 hrs treatment at 150° C., the refractive index of the resultant coating 1.782 at 30 nanometers thickness. After additional treatment for 6 hours at 450° C., the refractive index of the resultant coating was 2.122 at 27 nanometers thickness.

A 10 wt % solution of Al(OSi(CH₃)₂OSi(CH₃)₃)₃ in dry hexanes was spin coated on glass slide @ 2 krpm/30 sec. The substrate was heated for 30 min at 150° C. in air. A 150 nm thick transparent amorphous aluminum oxide layer was formed.

A 50 wt % solution of Al(OSi(CH₃)₂OSi(CH₃)₃)₃ in dry hexanes was spin coated on graphite slide @ 2 krpm/30 sec. The substrate was heated for 30 min at 150° C. in air. A 300 nm thick transparent amorphous aluminum oxide layer was formed.

A 50 wt % solution of Sn(OSi(CH₃)₂OSi(CH₃)₃)₄ in dry hexanes was spin coated on glass slide @ 2 krpm/30 sec. The substrate was heated 1 hour at 150° C. in air. A 500 nm thick transparent amorphous tin oxide layer was formed.

Example 12

Schottky Diode—ITO/TiOx/Au

A layer of Ti(OSi(CH₃)₂OSi(CH₃)₃)₄ was deposited onto ITO-coated, solvent and UV-ozone cleaned glass substrates via spin-coating liquid Ti(OSi(CH₃)₂OSi(CH₃)₃)₄ at 4 krpm/100 sec, and baked for 1 hour at 200° C. in air. A gold electrode (500 A) was evaporated onto the resulting TiOx layer using a shadow mask. The device was immersed in boiling water at pH 3 for about 10 minutes, and further dried in lab air. Current-voltage characteristics under both reversed and forward polarity bias were measured and rectification ratio of about 250 at bias voltage of 5V was observed. The rectification ratio of the device was found to be 10× higher than reported in the literature for nano-TiOx multiple coatings using conventional sol-gel process.[R. Konenkamp, Phys. Rev. B, vol. 61, 11057, 2000]

Example 13

Conductivity of ITO/polyoxide/Al

A 50 wt % hexane solution of a mixture of Ti(OSi(CH₃)₂OSi(CH₃)₃)₄ and VO(OSi(CH₃)₂OSi(CH₃)₃)₃ with Ti:V ratio 19:1 was prepared. The solution was spun onto ITO-coated, solvent and UV-ozone cleaned glass substrates at 2 krpm for 30 sec and baked for 15 min at 150° C. under inert atmosphere, to form a Ti(V)Oₓ layer of 250 nm thickness. The coated substrate was immersed in boiling water at pH 3 for 10 minutes, was then rinsed with deionized water, and was dried at 100° C. in air. An aluminum electrode (1000 A) was deposited via thermal evaporation onto formed (Ti:V)Oₓ layer using a shadow mask. Current-voltage characteristics for a pure TiO₂ layer, a Ti(V)Oₓ layer before hydrolysis, and the same after hydrolysis indicated a significant increase in out-of-plane conductivity for Ti(V)Oₓ, as compared with TiOₓ coatings without the vanadium component.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A compound of formula I

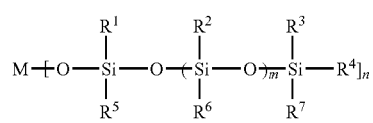

wherein
M is Al, Sn, Ga, In, Tl, Pb, or Ge;
R¹, R², R³, R⁴, R⁵, R⁶, and R⁷ are independently H, C₁-C₁₀ alkyl, phenyl or

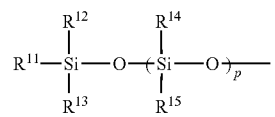

R¹⁰, R¹¹, R¹², R¹³, R¹⁴ and R¹⁵ are independently H, C₁-C₁₀ alkyl or phenyl;
n is equal to the value of the oxidation state of M;
m and p are independently 0 or an integer from 1 to 5.

2. A compound according to claim 1, wherein a Lewis base is coordinated to M.

3. A compound according to claim 1, wherein m and p are 0.

4. A compound according to claim 1, wherein M is Al, Ga, In, or Sn.

5. A compound according to claim 1, wherein M is Al or In.

6. A compound according to claim 1, wherein R¹, R², R³, R⁴, R⁵, R⁶, and R⁷ are independently H or methyl.

7. A compound according to claim 1, wherein R¹, R², R³, R⁴, R⁵, R⁶, and R⁷ are methyl.

8. A compound according to claim 1, of formula

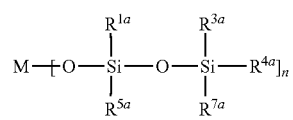

wherein R¹ᵃ, R³ᵃ, R⁴ᵃ, R⁵ᵃ, and R⁷ᵃ are H or methyl.

9. A compound according to claim 1, of formula $Sn(OSi(CH_3)_2OSi(CH_3)_3)_4$.

10. A compound according to claim 1, of formula $Al(OSi(CH_3)_2OSi(CH_3)_3)_3$.

11. A compound according to claim 1, of formula $In(OSi(CH_3)_2OSi(CH_3)_3)_3$.

* * * * *